US008933025B2

(12) United States Patent
Ishimaru et al.

(10) Patent No.: US 8,933,025 B2
(45) Date of Patent: Jan. 13, 2015

(54) AGENT FOR SUPPRESSING POSTPRANDIAL ELEVATION OF BLOOD INSULIN CONCENTRATION

(75) Inventors: Kotomi Ishimaru, Haga-gun (JP); Kazuhisa Sawada, Haga-gun (JP); Akira Shimotoyodome, Haga-gun (JP)

(73) Assignee: Kao Corporation, Tokyo (JP)

( * ) Notice: Subject to any disclaimer, the term of this patent is extended or adjusted under 35 U.S.C. 154(b) by 179 days.

(21) Appl. No.: 13/383,665

(22) PCT Filed: Jul. 16, 2010

(86) PCT No.: PCT/JP2010/062052
§ 371 (c)(1),
(2), (4) Date: Jan. 12, 2012

(87) PCT Pub. No.: WO2011/007865
PCT Pub. Date: Jan. 20, 2011

(65) Prior Publication Data
US 2012/0108506 A1 May 3, 2012

(30) Foreign Application Priority Data
Jul. 16, 2009 (JP) .................................. 2009-168090

(51) Int. Cl.
A61K 38/00 (2006.01)
A61K 31/785 (2006.01)
C08G 69/10 (2006.01)
(52) U.S. Cl.
CPC .............. *A61K 31/785* (2013.01); *C08G 69/10* (2013.01)
USPC .......................................................... 514/6.7
(58) Field of Classification Search
CPC ............ A61K 31/00; A61K 47/48315; A61K 31/785; C07K 1/1077; C07K 5/06026; C07K 5/0806
See application file for complete search history.

(56) References Cited

U.S. PATENT DOCUMENTS

| 4,232,007 A * | 11/1980 | Kajihara et al. ................ 514/7.4 |
| 6,669,971 B1 * | 12/2003 | Kato et al. ......................... 426/46 |
| 2007/0099827 A1 | 5/2007 | Uotani et al. |
| 2010/0022014 A1 | 1/2010 | Shimotoyodome et al. |

FOREIGN PATENT DOCUMENTS

| JP | 03-030648 A | 2/1991 |
| JP | 03-047087 A | 2/1991 |
| JP | 05-095767 A | 4/1993 |
| JP | 09-028309 A | 2/1997 |
| JP | 2005-200330 A | 7/2005 |
| JP | 2006-316022 A | 11/2006 |
| JP | 2007-022982 A | 2/2007 |
| JP | 2008-145136 | 6/2008 |
| JP | 2008-255063 A | 10/2008 |
| JP | 2009-173634 A | 8/2009 |
| WO | WO 2005/049050 A1 | 6/2005 |
| WO | WO 2007/043606 | 4/2007 |
| WO | WO 2009/035173 A1 | 3/2009 |
| WO | WO 2011/007863 A1 | 1/2011 |
| WO | WO 2011/007864 A1 | 1/2011 |

OTHER PUBLICATIONS

Bruckner et al. ,"Structure of Poly-D-glutamic Acid isolated from Capsulated Strains of B. anthracis", Nature, 1953, p. 508.*
Reiser et al., "Serum insulin and glucose in hyperinsulinemic subjects fed three different levels of sucrose"; The American Journal of Clinical Nutrition; 1984; pp. 2348-2358; see p. 2355.*
Grundy et al. , "Effectiveness and Tolerability of Simvastatin Plus Fenofibrate for Combined Hyperlipidemia (The SAFARI Trial)"; Am J Cardiol, 2005, pp. 462-468.*
Reiser et al., "Serum insulin and glucose in hyperinsulinemic subjects fed three different levels of sucrose", The American Journal of Clinical Nutrition, 1981, pp. 2348-2358.*
Kiuchi, "Miso & Natto", Food Culture, pp. 7-10; 2001.*
Food Culture, No. 3, 2001, cover page and pp. 2-3.*
Bastyr III et al.,"Therapy Focused on Lowering Postprandial Glucose, Not Fasting Glucose, May Be Superior for Lowering HbA1c", Diabetes Care 23:1236-1241, 2000.*
Sung et al.,"Natural and Edible Biopolymer Poly-_-glutamic Acid: Synthesis, Production, and Application"; The Chemical Record, vol. 5, 352-366; 2005.*
Taniguchi et al. "Natto and viscous vegetables in a Japanese style meal suppress postprandial glucose and insulin responses", Asia Pac J Clin Nutr ;2008;17 (4):663-668.*
Yamaguchi et al., "Detection of _-Polyglutamic Acid (g-PGA) by SDS-PAGE"; Biosci. Biotech. Biochem., 355-358, 1996.*
International Search Report (ISR) for PCT/JP2010/062052, I.A. fd: Jul. 16, 2010, mailed Sep. 14, 2010, from the Japanese Patent Office, Tokyo, Japan.
International Preliminary Report on Patentability (Chapter I of the Patent Cooperation Treaty) for PCT/JP2010/062052, I.A. fd: Jul. 16, 2010, issued Feb. 7, 2012, from the International Bureau of WIPO, Genera, Switzerland.
Karmaker, S. et al., "Antidiabetic Activity of the Orally Effective Vanadyl-Poly (-Glutamic Acid) Complex in Streptozotocin(STZ)-induced Type 1 Diabetic Mice," J Biomater Appl, 22: 449-464 (Mar. 2008), SAGE Publications, Los Angeles, CA.
Modan, M et al., "Hyperinsulinemia. A link between hypertension obesity and glucose intolerance," J Clin Invest 75(3): 809-817 (Mar. 1985), Am. Soc. for Clinical Investigation, Ann Arbor, MI.
Extended European search report for EP application No. 10799923.7, including the supplementary European search report and the European search opinion, dated Dec. 3, 2012, European Patent Office, Munich, Germany.
Notification of First Office Action for CN Patent Application No. 201080031674.8, mailed Sep. 10, 2012, from the Patent Office of the People's Republic of China, Beijing, China.
"Diabetes," Wei Liang et al., eds., p. 4, Inner Mongolia Science and Technology Press, China, Oct. 31, 2002.

* cited by examiner

*Primary Examiner* — Karlheinz R Skowronek
*Assistant Examiner* — Lianko Garyu
(74) *Attorney, Agent, or Firm* — Sterne, Kessler, Goldstein & Fox P.L.L.C.

(57) ABSTRACT

An agent for suppressing postprandial elevation of blood insulin concentration, comprising a polyglutamic acid as an active ingredient.

14 Claims, No Drawings

AGENT FOR SUPPRESSING POSTPRANDIAL ELEVATION OF BLOOD INSULIN CONCENTRATION

TECHNICAL FIELD

The present invention relates to an agent for suppressing postprandial elevation of blood insulin concentration.

BACKGROUND ART

Insulin is one of peptide hormones that are secreted from pancreatic β-cells in the pancreas, and acts to decrease an elevated blood glucose level and keep it at a normal level. Main physiological effects of insulin may include promotion of uptake of sugars, amino acids and the like and protein synthesis in the muscle tissue; and promotion of sugar uptake and utilization thereof, promotion of lipid synthesis, suppression of lipid decomposition or burning, and promotion of protein synthesis in the adipose tissue; and the like.

Secretion of insulin is mainly promoted by glucose. When sugar is uptaken into a body by meals or the like and a blood sugar level (blood glucose level) increases, insulin is secreted so as to decrease the elevated blood sugar level, as a result, the blood insulin level increases. Therefore, the secretion of insulin is very important for keeping a blood sugar level at a constant value to prevent diabetes mellitus.

On the other hand, it is known that continuous secretion of insulin under a state of hyperglycemia leads to decrease of insulin sensitivity (insulin resistance) in the skeletal muscles, liver and adipose tissue that are target organs for insulin. When insulin resistance occurs, insulin is secreted more from the pancreas so as to compensate for insufficiency in an effect of decreasing blood sugar. When such excess secretion of insulin is repeated, the pancreas gets exhausted, and finally the ability of secreting insulin from pancreatic β-cells is decreased, while keeping higher insulin resistance in the target organs. The above functional deterioration of regulatory mechanism of insulin in the body may leads to development of lifestyle diseases such as diabetes mellitus, and further obesity, Type II diabetes mellitus (hypertension) and the like (see Non-patent Literature 1).

Until today, it has been considered that an amount of insulin secretion in the blood varies depending on blood sugar levels, i.e., uptake amounts of carbohydrates. However, in recent years, it has been newly reported that lipid uptake also correlates the elevation of blood insulin level as well as carbohydrate uptake (see Patent Literature 1). According to Patent Literature 1, it was confirmed that when carbohydrates and lipids are uptaken together, a secretion amount of insulin is excessively higher than that of when carbohydrates are uptaken solely. Further, it was also confirmed that the excess secretion of insulin due to such simultaneous ingestion of carbohydrates and lipids is a factor which is highly correlated to obesity.

In recent years, eating habits of Japanese has been westernized, and meals have been changed from conventional meals including mainly carbohydrates to meals rich in lipids. As a result of such change in eating habits, increase in lifestyle diseases and metabolic syndrome has become a problem. Therefore, it is important to prevent and improve adverse effects of high fat diets on health.

In order to prevent diabetes mellitus, various approaches for suppressing elevation of blood sugar levels have been made. For example, Patent Literature 2 suggested an agent for improving blood sugar levels using polyglutamic acids so as to suppress elevation of blood sugar levels. Polyglutamic acids are widely used as moisturizing agents, absorbing agents and the like due to their high water retaining ability, and gain attentions as biodegradable polymers. Further, it was reported that polyglutamic acids have an effect of promoting absorption of calcium from the small intestine, an effect of suppressing elevation of blood pressure, and an effect of promoting saliva secretion (for example, see Patent Literatures 3 to 5).

However, under the current circumstance, almost no active effort is undertaken for suppressing elevation of blood insulin concentration.

PRIOR ART LITERATURE

Patent Literatures

Patent Literature 1: JP-A-2008-145136 ("JP-A" means unexamined published Japanese patent application)
Patent Literature 2: JP-A-2005-200330
Patent Literature 3: JP-A-5-95767
Patent Literature 4: JP-A-2008-255063
Patent Literature 5: WO 2005/049050
Non-Patent Literature 1: Modan M. et al., J. Ckin. Invest., 1985 March; 75(3):809-17

SUMMARY OF INVENTION

Technical Problem

The present invention is contemplated for providing an agent for suppressing postprandial elevation of blood insulin concentration, which can suppress excess elevation of blood insulin concentration that occurs when carbohydrates and lipids are simultaneously ingested. Further, the present invention is also contemplated for providing an agent for suppressing postprandial elevation of blood insulin concentration, which is useful for preventing or improving obesity and diabetes mellitus that are caused by excess elevation of insulin concentration in the blood.

Furthermore, the present invention is contemplated for providing an agent for suppressing postprandial elevation of blood insulin concentration, which is useful for medicinal use and food application. Specifically, the present invention is contemplated for providing an agent for suppressing postprandial elevation of blood insulin concentration, which suppresses excess elevation of insulin concentration after eating and is thereby useful for medicinal use or food application as non-medicinal use for decreasing risks of development of, preventing, improving, alleviating or treating obesity and diabetes mellitus.

Solution to Problem

In view of the above-mentioned problem, the present inventors have made extensive studies. As a result, they have found that polyglutamic acids have an effect of suppressing postprandial elevation of blood insulin concentration. The present invention has been completed based on this finding.

The present invention provides the following means.
(1) An agent for suppressing postprandial elevation of blood insulin concentration, comprising a polyglutamic acid as an active ingredient.
(2) A polyglutamic acid for use in the suppression of postprandial elevation of blood insulin concentration.
(3) A method of suppressing postprandial elevation of blood insulin concentration, comprising administering a polyglutamic acid.

(4) Use of a polyglutamic acid for the preparation of a medicament having an effect of suppressing postprandial elevation of blood insulin concentration.

Advantageous Effects of Invention

According to the agent for suppressing postprandial elevation of blood insulin concentration of the present invention, elevation of insulin concentration, in particular excess elevation of insulin concentration after eating (more specifically, elevation of insulin concentration which occurs when carbohydrates and lipids are simultaneously ingested), can be decreased. Furthermore, the agent for suppressing postprandial elevation of blood insulin concentration of the present invention can suppress undue elevation of insulin concentration and regulate effects of insulin in the body after eating within a normal level, and is thereby useful for decreasing risks of development of, preventing, improving, alleviating or treating obesity and diabetes mellitus.

Other and further features and advantages of the invention will appear more fully from the following description.

MODE FOR CARRYING OUT THE INVENTION

Hereinafter, the present invention is described in detail.

The agent for suppressing postprandial elevation of blood insulin concentration of the present invention contains a polyglutamic acid as an active ingredient. The structural formula of the polyglutamic acid used in the present invention is represented by $(-NH-CH(COOH)-CH_2-CH_2-CO-)_n$.

As shown in the Examples mentioned below, the polyglutamic acid has an effect to significantly suppress elevation of insulin concentration in the blood. Therefore, the polyglutamic acid can be used as an agent for suppressing elevation of insulin concentration in the blood, and can also be used for the preparation of an agent for suppressing elevation of insulin concentration.

Until now, it has not been known that the polyglutamic acid has the effect of suppressing postprandial elevation of blood insulin concentration. And also, it has not been known that the polyglutamic acid has the effect of preventing or improving obesity.

As shown in the Examples mentioned below, the polyglutamic acid used in the present invention has the effect to suppress elevation of insulin concentration, in particular excess elevation of insulin concentration after eating.

In the present invention, the "effect of suppressing elevation of blood insulin concentration" encompasses both an effect of suppressing secretion of insulin in which elevation of blood insulin concentration is suppressed by suppressing secretion of insulin from the pancreas, and an effect of decreasing insulin in which elevation of blood insulin concentration is suppressed by decreasing the blood insulin concentration.

Furthermore, the "suppressing postprandial elevation of blood insulin concentration" means suppression of excess elevation of blood insulin concentration caused by uptaking lipids and carbohydrates. As used herein, the "excess elevation of blood insulin concentration" refers to elevation of blood insulin concentration after eating being higher than elevation of blood insulin concentration when only carbohydrates are uptaken. In the present invention, "uptaking lipids and carbohydrates" means that a lipid and a carbohydrate are uptaken under a condition that causes excess elevation of blood insulin concentration, and includes naturally the case when a carbohydrate and a lipid are uptaken simultaneously, and also the case when they are uptaken separately with an interval of about 4 hours.

The lipid in the present invention is not specifically limited as long as it is a lipid component that is included in a general meal and enhances secretion of insulin, and specific examples may include butter, lard, fish oil, corn oil, rapeseed oil, olive oil, sesame oil and the like.

The carbohydrate in the present invention is net specifically limited as long as it is a carbohydrate component that is included in a general meal and promotes secretion of insulin, and specific examples may include rice, starch, wheat flour, sugar, fructose, glucose, glycogen and the like.

Although uptake amounts of the lipid and carbohydrate that cause excess elevation of blood insulin concentration vary depending on the composition of a meal, differences among individuals, and the like, the amounts are generally 5 g/60 kg body weight or more for the lipid and 10 g/60 kg body weight or more for the carbohydrate as uptaking amounts per each meal.

As is shown in the Examples mentioned below, although the effect of suppressing postprandial elevation of blood insulin concentration by the polyglutamic acid was observed in all polyglutamic acids regardless of their molecular weights, the polyglutamic acid having a larger molecular weight to some extent showed a more excellent effect of suppressing postprandial elevation of blood insulin concentration.

As a result, the molecular weight of the polyglutamic acid used in the present invention is preferably a weight average molecular weight of about 9,000 or more, more preferably of 28,000 or more, in order to suppress postprandial elevation of blood insulin concentration more effectively.

On the other hand, when the agent for suppressing postprandial elevation of blood insulin concentration of the present invention is used in the form of an oral liquid preparation, it is preferable that the preparation has a comparatively lower viscosity from the viewpoints of production, and of feeling of the throat, slimy feeling and easiness of swallowing during drinking, and the like. Therefore, the upper limit of the weight average molecular weight of the polyglutamic acid is preferably about 5,000,000, more preferably about 800,000. From the viewpoints of the effect of suppressing postprandial elevation of blood insulin concentration, the weight average molecular weight of the polyglutamic acid is preferably from 9,000 to 5,000,000, more preferably from 28,000 to 5,000,000. From the viewpoint of viscosity, the weight average molecular weight of the polyglutamic acid is preferably from 9,000 to 5,000,000, more preferably from 9,000 to 800,000. From both of the viewpoints of the effect of suppressing postprandial elevation of blood insulin concentration and of viscosity, the weight average molecular weight of the polyglutamic acid is preferably from 9,000 to 5,000,000, more preferably from 28,000 to 800,000. The weight average molecular weight can be measured by, for example, high performance liquid chromatography using a gel permeation column.

The polyglutamic acid used in the present invention can be produced by a chemical synthesis or can be generated by a microorganism, or a commercial product can also be used. Further, the optical activity of glutamic acid that constitutes the polyglutamic acid may be a D- or L-form, or a mixture thereof. A natural polyglutamic acid is a polymer that is formed by binding of glutamic acid at the γ-position, and it can be obtained by culturing wild type microorganisms having an ability to produce a polyglutamic acid, or microorganisms given an ability to produce a polyglutamic acid by gene recombination, or the like. Examples of wild type microorganisms that produce a polyglutamic acid may include a part of *Bacillus* bacteria including *Bacillus subtilis* var. *natto* and related species thereof (*Bacillus subtilis* var. *chunqkookjanq*, *Bacillus licheniformis*, *Bacillus megaterium*, *Bacillus anthracis*, *Bacillus halodurans*), *Natrialba aegyptiaca*, *Hydra* and the like (Ashiuchi, M., et al.: Appl. Microbiol. Biotechnol., 59, pp. 9-14 (2002)). As examples of the production of a polyglutamic acid using a gene recombination technique, it has been known that a recombinant *Bacillus subtilis* ISW1214 strain, which was constructed by gene transfer with a plasmid, produced the polyglutamic acid at about 9 g/L/5 days (Ashiuchi, M., et al.: Biosci. Biotechnol. Biochem., 70, pp. 1794-1797 (2006)), and a recombinant *E. coli*, which was constructed by gene transfer with a plasmid, produced the polyglutamic acid at about 4 g/L/1.5 days (Jiang, H., et al.: Biotechnol. Lett., 28, pp. 1241-1246 (2006)). Furthermore, polyglutamic acids are commercially produced as food additives, materials for cosmetics and thickening agents, and the like, and it is also possible to purchase polyglutamic acids that are supplied by domestic or foreign manufacturers of polyglutamic acids (for example, domestic manufacturers: Nippon Poly-Glu Co., Ltd., Ichimaru Pharcos Co., Ltd., Meiji Food Materia Co., Ltd. and the like, foreign manufacturers: BioLeaders Corporation and the like).

The polyglutamic acid used in the present invention may be a salt thereof. Examples of the salt may include alkali metal salts such as sodium salts and potassium salts; alkaline earth metal salts such as magnesium salts and calcium salts; ammonium salts; ethanolamine salts; basic amino acid salts and the like, and the salt is not specifically limited as long as it can be used for medical or food application.

In the present invention, the above-mentioned polyglutamic acid can be used as an agent for suppressing postprandial elevation of blood insulin concentration itself. Alternatively, the polyglutamic acid may be used after adding a suitable liquid or solid excipient or bulking agent such as titanium oxide, calcium carbonate, distilled water, lactose and starch. In this case, although the content of the polyglutamic acid is not specifically limited, it is included by preferably from 0.01 to 100% by mass, particularly preferably from 0.1 to 80% by mass in the agent for suppressing postprandial elevation of blood insulin concentration.

When the agent for suppressing postprandial elevation of blood insulin concentration is used for use in foods, medicaments or the like, the polyglutamic acid can be solely administered to humans and animals by gastrointestinal administration, intraperitoneal administration, intravascular administration, intradermal administration, subcutaneous administration or the like, or can be ingested as a form of various foods, medicinal products, pet foods or the like, all of which incorporates the polyglutamic acid. As the food, it is possible to apply to general foods, as well as to foods such as cosmetic foods, foods for diseased persons and foods for specified health use, which have the concepts of suppressing elevation of insulin concentration in the blood, and of decreasing the risks of development of, preventing, improving, alleviating or treating obesity and diabetes mellitus, and indicate that effect as necessary. In the case of use as a medicinal product, the agent can be formed into an oral solid formulation such as a tablet and a granule agent, or an oral liquid formulation such as an oral liquid agent and a syrup agent.

When the oral solid formulation is to be prepared, a tablet, a coated tablet, a granular agent, a powder agent, a capsule agent or the like can be produced by a conventional method after adding an excipient, and if needed, a binder, a disintegrating agent, a lubricating agent, a coloring agent, a taste masking agent, a flavoring agent and the like to a polyglutamic acid. Alternatively, when the oral liquid formulation is to be prepared, an oral liquid agent, a syrup agent, an elixir agent or the like can be prepared by a conventional method by adding a taste masking agent, a buffering agent, a stabilizer, a taste masking agent and the like.

Although the content of the polyglutamic acid in each of the above-mentioned formulations and agents is not specifically limited, the content is preferably from 0.01 to 100% by mass, particularly preferably from 0.1 to 80% by mass.

The effective administration (ingestion) amount of the polyglutamic acid in each of the above-mentioned formulations and agents is preferably from 0.01 to 1.0 g/kg body weight per day. The agent for suppressing postprandial elevation of blood insulin concentration of the present invention can be effectively used before, during or after eating, and it is preferably used before or during eating.

Subjects of administration or ingestion are not specifically limited as long as the subject is a person in need thereof. It is preferable that the subject is a person having a fasting blood sugar level of 100 mg/dL or more, or having a fasting blood triglyceride level of 100 mg/dL or more.

EXAMPLES

Hereinafter, the present invention will be described more in detail with reference to Examples, but the present invention is not limited thereto.

Preparation Example 1

Preparation of Polyglutamic Acid Having Weight Average Molecular Weight of 190,000

Using a commercially available polyglutamic acid having a weight average molecular weight of 800,000 (manufactured by Meiji Food Materia Co., Ltd) as a starting material, 500 mL of a 3 w/w % aqueous solution of the polyglutamic acid was prepared. The pH of this solution was adjusted to 2 with hydrochloric acid, and the temperature was set to constant at 70° C. At 3 hours after the initiation of the setting to a constant temperature, the solution was neutralized to pH 7 by using an aqueous sodium hydroxide solution, and concentrated by using an ultrafiltration membrane having an exclusion limit of 300 k (type: PBMK, manufactured by Millipore). At that time, washing by adding water was suitably conducted with distilled water of a three-fold amount of the sample before concentration, and a 10-fold concentrate was subjected to lyophilization. A molecular weight of the sample after lyophilization was measured by an HPLC method as shown in the measurement examples mentioned below. As a result, 1.7 g of a polyglutamic acid having a weight average molecular weight of 190,000 was obtained.

Preparation Example 2

Preparation of Polyglutamic Acid Having Weight Average Molecular Weight of 70,000

Using a commercially available polyglutamic acid having a weight average molecular weight of 800,000 (manufactured by Meiji Food Materia Co., Ltd.) as a starting material, 500 mL of a 3 w/w % aqueous solution of the polyglutamic acid was prepared. The pH of this solution was adjusted to 2 with hydrochloric acid, and the temperature was set to constant at 70° C. At 6 hours after the initiation of the setting to a constant temperature, the solution was neutralized to pH 7 by using an aqueous sodium hydroxide solution, and concentrated by using an ultrafiltration membrane having an exclusion limit of 100 k (type: PBHK, manufactured by Millipore). At that time, washing by adding water was suitably conducted with distilled water of a three-fold amount of the sample before concentration, and a 10-fold concentrate was subjected to lyophilization. A molecular weight of the sample after lyophilization was measured by an HPLC method as shown in the measurement examples mentioned below. As a result, 8.3 g of a polyglutamic acid having a weight average molecular weight of 70,000 was obtained.

Preparation Example 3

Preparation of Polyglutamic Acid Having Weight Average Molecular Weight of 28,000

Using a commercially available polyglutamic acid having a weight average molecular weight of 800,000 (manufactured by Meiji Food Materia Co., Ltd.) as a starting material, 500 mL of a 3 w/w % aqueous solution of the polyglutamic acid was prepared. The pH of this solution was adjusted to 2 with hydrochloric acid, and the temperature was set to constant at 70° C. At 8 hours after the initiation, the temperature was changed to 90° C. At 11 hours after the initiation of the setting to a constant temperature, the solution was neutralized to pH 7 by using an aqueous sodium hydroxide solution, and concentrated by using an ultrafiltration membrane having an exclusion limit of 50 k (type: PBQK, manufactured by Millipore). At that time, washing by adding water was suitably conducted with distilled water of a three-fold amount of the sample before concentration, and a 10-fold concentrate was subjected to lyophilization. A molecular weight of the sample after lyophilization was measured by an HPLC method as shown in the measurement examples mentioned below. As a result, 6.3 g of a polyglutamic acid having a weight average molecular weight of 28,000 was obtained.

Quantitative Analysis and Measurement of Molecular Weight of Polyglutamic Acid

The quantitative analysis of the polyglutamic acid and measurement of molecular weight of the polyglutamic acid were performed by an HPLC analysis using TSKGel G4000PWXL and TSKGel G6000PWXL gel permeation columns (trade names, manufactured by Tosoh Corporation). The analysis conditions were that 0.1 M sodium sulfate was used as an eluent, and that the flow rate was 1.0 mL/min, the column temperature was 50° C. and the UV detection wavelength was 210 nm. For verification of concentrations, a calibration curve was prepared by using a polyglutamic acid having a molecular weight of 800,000 (manufactured by Meiji Food Materia Co., Ltd.). For verification of molecular weights, polyglutamic acids having various different molecular weights (those manufactured by Wako Pure Chemical Industries, Ltd. (162-21411 and 162-21401)), SIGMA-ALDRICH (P-4886 and P-4761) and Meiji Food Materia Co., Ltd. (molecular weight: 880,000)) were used, and weight average molecular weights thereof had been obtained in advance by using pullulan (trade name: Shodex STANDRD P-82, manufactured by Showa Denko K.K.).

Test Example 1

Effect of Polyglutamic Acid to Suppress Elevation of Insulin Concentration

As polyglutamic acids (PGAs), six kinds of samples having weight average molecular weights of 9,000, 350,000 and 800,000 (manufactured by Meiji Food Materia Co., Ltd.) and of 28,000, 70,000 and 190,000 (prepared in Preparation Examples 1 to 3) were used.

Furthermore, the following experiments were performed by using eight 8-week-old male mice (C57BL/6J Jcl: manufactured by Clea Japan, Inc.) for each group.

1. Preparation of Oral Administration Samples

An emulsion liquid was prepared by emulsifying glucose (manufactured by Kanto Kagaku) and triolein (Glyceryl trioleate: manufactured by Sigma) by using lecithin (made from eggs, manufactured by Wako Pure Chemical Industries) and albumin (derived from bovine serum, manufactured by Sigma). A sample for oral administration was prepared by adding the polyglutamic acid sample to this emulsion liquid so that the final concentrations became 5 (w/w) % of the polyglutamic acid, 5 (w/w) % of glucose, 5 (w/w) % of triolein, and 0.2 (w/w) % of lecithin and 1.0 (w/w) % of albumin in the emulsifying agent. Furthermore, a sample in which water had been added instead of the polyglutamic acid was prepared as a control sample.

2. Oral Administration Tests

The initial blood sampling was performed on a mouse that had been food-deprived overnight by using a heparin-treated hematocrit capillary (manufactured by VITREX) from the orbital vein under ether anesthesia. Thereafter, the oral administration sample was administered orally by using a feeding needle, and the blood was collected from the orbital vein under ether anesthesia at after 10 minutes, 30 minutes, 1 hour and 2 hours. The amount of oral administration against the mouse is shown in the following Table 1.

TABLE 1

| | Amount of oral administration in mouse | | |
|---|---|---|---|
| | Glucose (mg/1 g body weight) | Triolein (mg/1 g body weight) | Polyglutamic acid (mg/1 g body weight) |
| Control group | 2 | 2 | — |
| Polyglutamic acid administered group | 2 | 2 | 2 |

The blood collected by the heparin-treated hematocrit capillary was stored under ice-cooling until blood plasma separation, and centrifuged at 11,000 rpm for 5 minutes to give blood plasma. A blood insulin concentration in the obtained plasma was measured by using a Insulin measurement kit (manufactured by Morinaga Institute of Biological Science, Inc., ELISA method).

The blood insulin concentrations up to 2 hours after the oral administration of the sample were measured, as a result, it was found that the concentration of the blood insulin was the maximum at 10 minutes after the administration. Therefore, the difference (A value) between the maximum value (at 10 minutes after the administration) and the initial value (at the time of the initial blood sampling) of the blood insulin concentration was defined as the maximum insulin concentration elevation, and is shown in Table 2.

Further, the statistically-significant difference between the groups was also considered based on the obtained values of the maximum insulin concentration elevation, and is shown in Table 2. When significance ($p<0.05$) was recognized by an analysis of variance, significant difference between the groups was determined by a verification between the polyglutamic acid-administered groups (weight average molecular weights: 9,000, 28,000, 70,000, 190,000, 350,000 and 800,000) and the control group using a multiple comparison test (Bonferroni/Dunn method). From the obtained result, significance was judged with considering p<0.05 as a significant difference.

TABLE 2

Maximum insulin concentration elevation in mouse;
(10-minute value-initial value) (analysis of variance P < 0.05)

| | Maximum insulin concentration elevation Average ± S.E. (ng/ml) | Significant difference against control group |
|---|---|---|
| Control group | 5.40 ± 0.80 | — |
| Polyglutamic acid administered group (weight average molecular weight: 9,000) | 3.75 ± 0.30 | N.S. |
| Polyglutamic acid administered group (weight average molecular weight: 28,000) | 2.42 ± 0.45 | P < 0.05 |
| Polyglutamic acid administered group (weight average molecular weight: 70,000) | 1.95 ± 0.32 | P < 0.05 |
| Polyglutamic acid administered group (weight average molecular weight: 190,000) | 2.82 ± 0.45 | P < 0.05 |
| Polyglutamic acid administered group (weight average molecular weight 350,000) | 2.71 ± 0.65 | P < 0.05 |
| Polyglutamic acid administered group (weight average molecular weight: 800,000) | 1.72 ± 0.24 | P < 0.05 |

*) S.E.: Standard Error
*) N.S.: Not Significant

As is apparent from the results shown in Table 2, the values of the maximum insulin concentration elevation in the polyglutamic acid-administered groups (weight average molecular weights: 9,000, 28,000, 70,000, 190,000, 350,000 and 800,000) were lower than that of the control group. Specifically, the values of the maximum insulin concentration elevation in the polyglutamic acid-administered groups having weight average molecular weights of 28,000, 70,000, 190,000, 350,000 and 800,000 were significantly lower than that of the control group. Thus, it was found that a polyglutamic acid having a higher molecular weight has a more excellent effect of suppressing postprandial elevation of insulin concentration in the blood.

Furthermore, as mentioned above, it is known that undue elevation of insulin concentration causes insulin resistance, and eventually leads to obesity and diabetes mellitus. Therefore, the above-mentioned polyglutamic acids can effectively suppress excess secretion of insulin, and thereby can be preferably used for the prevention or improvement of obesity and diabetes mellitus.

INDUSTRIAL APPLICABILITY

The agent for suppressing postprandial elevation of blood insulin concentration of the present invention is useful for preventing or improving obesity and diabetes mellitus, and can be utilized in the fields of functional foods, medicinal products and medical treatments.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2009-168090 filed in Japan on Jul. 16, 2009, which is entirely herein incorporated by reference.

The invention claimed is:

1. A method of suppressing postprandial elevation of blood insulin concentration in a subject that has a fasting blood sugar level of 100 mg/dL or more, and, that is eating both carbohydrate and lipid within a 4 hour interval of each other, comprising administering, to said subject, an effective amount of a polyglutamic acid that has a weight average molecular weight of 190,000 to 5,000,000,
   wherein the polyglutamic acid is administered in a solid or liquid composition that either consists of polyglutamic acid or comprises a polyglutamic acid formulation,
   and wherein the effective amount is 0.01 to 1.0 g of polyglutamic acid per kilogram (kg) body weight of said subject per day.

2. The method of claim 1, wherein said polyglutamic acid has a weight average molecular weight of 190,000 to 800,000.

3. The method of claim 1, wherein said polyglutamic acid has a weight average molecular weight of 190,000 to 350,000.

4. The method of claim 1, wherein said polyglutamic acid has a weight average molecular weight of 190,000.

5. The method of claim 1, wherein said polyglutamic acid has a weight average molecular weight of 350,000.

6. The method of claim 1, wherein said polyglutamic acid has a weight average molecular weight of 350,000 to 800,000.

7. The method of claim 1, wherein said polyglutamic acid is administered in the form of a food.

8. The method of claim 1, wherein said subject is a human.

9. The method of claim 1, wherein said subject is a non-human animal.

10. The method of claim 1, wherein said administering occurs during or before the eating.

11. The method of claim 1, wherein said administering occurs during the eating.

12. The method of claim 8, wherein said human is eating a meal that comprises 5 g/60 kg body weight or more of lipid and 10 g/60 kg body weight or more of carbohydrate.

13. The method of claim 1, wherein said subject is eating a meal that comprises 5 g/60 kg body weight or more of lipid and 10 g/60 kg body weight or more of carbohydrate.

14. The method of claim 1, wherein said polyglutamic acid is administered in the form of an oral liquid preparation.

* * * * *